(12) United States Patent  
Shubinsky et al.

(10) Patent No.: US 7,948,617 B2  
(45) Date of Patent: May 24, 2011

(54) OPTICAL MULTIWAVELENGTH WINDOW CONTAMINATION MONITOR FOR OPTICAL CONTROL SENSORS AND SYSTEMS

(75) Inventors: Gary Shubinsky, Buffalo Grove, IL (US); Sam Paris, Chicago, IL (US)

(73) Assignee: Fluke Corporation, Everett, WA (US)

( * ) Notice: Subject to any disclaimer, the term of this patent is extended or adjusted under 35 U.S.C. 154(b) by 194 days.

(21) Appl. No.: 12/170,308

(22) Filed: Jul. 9, 2008

(65) Prior Publication Data

US 2009/0015824 A1 Jan. 15, 2009

Related U.S. Application Data

(60) Provisional application No. 60/948,662, filed on Jul. 9, 2007.

(51) Int. Cl.
*G01N 21/00* (2006.01)
(52) U.S. Cl. .................. 356/237.1; 356/239.7
(58) Field of Classification Search .... 356/237.1–237.5, 356/239.1–239.8, 240.1, 429–431; 250/223 B
See application file for complete search history.

(56) References Cited

U.S. PATENT DOCUMENTS

| | | | | |
|---|---|---|---|---|
| 4,428,673 A * | 1/1984 | Yoshida | | 359/599 |
| 5,220,400 A * | 6/1993 | Anderson et al. | | 356/240.1 |
| 5,812,270 A * | 9/1998 | Hampton et al. | | 356/394 |
| 6,765,206 B2 * | 7/2004 | Sugiyama et al. | | 250/330 |
| 2007/0263206 A1* | 11/2007 | LeBlanc et al. | | 356/239.7 |
| 2008/0062422 A1* | 3/2008 | Thomas et al. | | 356/432 |

* cited by examiner

*Primary Examiner* — Hoa Q Pham
(74) *Attorney, Agent, or Firm* — Fredrikson & Byron, P.A.

(57) ABSTRACT

A foreign-particle detection system for use with an optical instrument having a transmissive window with a first side and a second side includes a radiation source to emit a radiation signal, a diffusing reflector to diffusively spread the radiation signal emitted by the radiation source over the first side of the transmissive window, a radiation detector to detect, at the second side of the transmissive window, the diffusively spread radiation signal transmitted by the transmissive window, and to generate a detected radiation signal based on the detected diffusively spread radiation signal, and a computation module communicatively coupled to the radiation detector to detect a presence of foreign particles on at least one of the first side or the second side of the transmissive window based on at least the detected radiation signal.

32 Claims, 9 Drawing Sheets

OPTICAL MULTIWAVELENGTH WINDOW CONTAMINATION MONITOR FOR OPTICAL CONTROL SENSORS AND SYSTEMS

CROSS REFERENCE TO RELATED APPLICATIONS

This application claims benefit of the U.S. Provisional Application No. 60/948,662 entitled "Optical Multiwavelength Window Contamination Monitor for Optical Control Sensors and Systems," filed Jul. 9, 2007, the disclosure of which is hereby expressly incorporated herein by reference.

FIELD OF THE INVENTION

The disclosure generally relates to optical instrumentation and, more particularly, to a system and method of detecting contamination of a transmitting path of an optical measuring device.

DESCRIPTION OF THE RELATED ART

Optical instrumentation is extensively used in various industrial, military, and commercial applications. Recent advances in the field of robotics have further spurred the proliferation of optical devices capable of detecting and processing various forms of electromagnetic radiation. In some applications, optical instruments may be designed to detect electromagnetic radiation in the visible optical range. In other applications, optical instruments may operate with shorter wavelengths, such as those in the ultraviolet range. Optical measurements may also be used to detect longer wavelengths in the infrared part of the spectrum. Some examples of such non-contact temperature measurement devices are infrared radiometers, infrared imagers, infrared flame detectors, and infrared gas measurement sensors.

Optical instruments generally have a front window, or lens, for receiving electromagnetic radiation and for providing additional protection to the front-end optical components. These instruments may yield inaccurate readings if dust, debris, or other foreign materials contaminate this front window. In case of the safety- and process-critical applications, these inaccuracies may expose an operator to some dangerous conditions. In the case of process control applications, front window contamination will not only compromise the functional performance of the optical instrument but also impact various process control functions which rely on the accuracy of the instrument. The problem of window contamination is particularly prevalent in those industrial environments where dust, soot, water or oil droplets are present as a part of an operating environment and/or generated as a by-product of the process requiring optical measurements. Because window contamination is unavoidable in these environments, operators and technicians require reliable methods of detecting contamination in a timely fashion. In the field of non-contact temperature sensing instrumentation (Infrared radiometers), to take one example, it is important to have a radiometer that can reliably provide a highly accurate target temperature measurement. Some level of window contamination will directly impact the accuracy of such instruments, thus resulting in incorrect temperature readings and inaccurate control functions. Moreover, knowing the precise level of window contamination may be useful in correcting the output of the optical instrument by making the necessary adjustments in the signal acquisition processing.

Quite often, operators physically approach optical instruments in order to inspect the front window. Clearly, this type of inspection takes a significant amount of time and requires a human presence in close proximity to the process control area. Further, the level of skill and diligence of a particular operator may introduce additional uncertainties and even errors into the process of detecting, and cleaning of window contaminants. Still further, because optical process control and monitoring devices are frequently positioned in places that may be extremely dangerous and harmful to an operator, it is highly desirable to keep the process of inspection and cleaning of optical device windows to a minimum.

In addition to posing a high risk to human safety, window contamination and the related maintenance may be associated with high costs. For example, optical measuring devices are widely used as a key control sensors in reheat furnaces, glass float lines, metal processing operations, kilns, coke furnaces. Similarly, petroleum processing plants and chemical plants extensively use optical instrumentation with windows or lenses susceptible to contamination. In order to properly service an optical device, these facilities need to shut down at least part of the operation. Because most modern plants and factories operate twenty four hours a day, the accumulative cost of process stoppage and re-starting may cost hundreds of thousands, if not millions, of dollars. Additionally, stoppage time may cause significant damage to partially processed materials and may render part of the output of a plant defective. For example, if molten metal or metal alloy such as steel is allowed to cool down at an unexpected stage of the process, some of the metal may have to be discarded, thus raising the cost of optical window maintenance even higher.

There have been several attempts in the past to address the problem of automatically detecting foreign particles on the surface of a window of an optical device. For example, a method involving an off-axis mirror, an emitter, and a detector is described in the U.S. Pat. No. 5,812,270 to Hampton et al., and assigned to Ircon, Inc. In particular, this reference suggests positioning the off-axis mirror behind the window relative to the light incident from a target object. The reference then suggests directing the light from the emitter through the window in the direction of the mirror so that the light is reflected back through the window and toward the detector. The intensity of the light received by the detector is compared to the intensity of the light at the emitter in order to detect possible contamination. However, this method cannot provide a complete coverage of the surface of the window, thus providing only a partial information regarding the condition of the window. Furthermore, the accuracy of this method will be significantly impacted if the mirror itself is contaminated or partially covered by the dirt or debris.

Another known approach to detecting contamination of a window involves suspending an external illuminator directly in front of the window relative to the light incident from the target object, placing a detector inside the device and behind the window, and measuring the amount of light passing through the window. Unfortunately, this approach also has some significant shortcomings. In particular, the external illuminator obscures the optical path of the optical device. Additionally, the external illuminator itself may accumulate dust particles or other forms of contamination. Currently available solutions are based on a measurement of the intensity of radiation emitted by the reference source at a spectral region defined by a selected source/detector combination. Accurate and meaningful absolute intensity measurement is limited to various uncertainties and changes of both the reference source and the detector. If the reference source is external to the body of the instrument, then one of the main uncertainties if the external source is also contaminated by the same dust. If the reference source id is internal to the instrument, then a comparison between the reference measurement (clean window) and field measurements (dirty window) is also impacted by the ambient temperature stability of the source, ambient temperature stability of the detector and optical alignment of these two key devices.

In accordance with yet another known solution, light is generated within an optical device and is directed, via a protruded fiber optic light pipe, toward the window from the target object side. A detector similarly measures the value of absolute intensity of light passing through the window. However, this approach also provides only partial coverage of the window. Similarly to the solution involving an illuminator suspended directly in front of the window, and an external mirror the fiber optic light pipe is also prone to contamination. Moreover, the fiber optic tip is fragile and thus reduces the durability of the apparatus.

In general, the solutions known in the art share several additional limitations. Specifically, all of the available methods and systems have high margins of error due to the potential changes in the environment and none of the solutions teaches an effective method of addressing these additional factors. Because the spectral qualities of some of the elements used in these solutions vary with temperature and age, carrying out calculations related to the transmission of electromagnetic radiation with a high degree of accuracy becomes a relatively complicated task. For example, the spectral qualities of a window of an optical device may be significantly influenced by the environmental factors and, if these changes are ignored, the detection of contaminants may not always be accurate.

SUMMARY

In one embodiment, an optical device has at least two light sources capable of separately emitting electromagnetic radiation of at least two substantially different wavelengths (as an example, one source which produces radiation in the visible (or UV) part of the spectrum and another source which produces radiation in the near infrared region of the spectrum), a diffusely or partially diffusely coated crown designed to reflect the reference radiation across the entrance window or objective lens in a uniform manner, and one or more radiation detectors. In operation, the reference light source directs a modulated radiation signal first at a first wavelength and then directs a modulated radiation signal at a second wavelength toward the inner surface of the crown reflector, with the reflector spreading the reflected radiation over the entire surface of the window. The optical detector detects the reflected modulated radiation of each of the two wavelengths after the radiation signal passes through the window. The instrument detects the degree of the window contamination on the surface of the window by taking a ratio of the signal detected at the first wavelength to the signal detected at the second wavelength.

In another embodiment, the optical instrument has a plurality of light sources uniformly placed around the perimeter of the window. In another embodiment, the optical instrument is equipped with a ring illuminator adapted to emit light of at least two different wavelengths. In another embodiment, the multiple light sources are activated and deactivated sequentially with a short interval between the periods during which each light source emits a radiation signal.

In another aspect, the device has a housing, a light source positioned inside the housing, and a crown positioned outside the housing and on the opposite side of the light source. In another aspect, the curvature of the crown is suitable for diffusing light incident on the internal surface of the crown in the direction of the window facing the internal surface of the crown and surrounded by the rim of the crown. In one embodiment, the crown is made of metal, plastic, or glass. In another embodiment, the crown has an internal machined, chemically etched or sandblasted surface. In another embodiment, the internal surface is coated to achieve a diffused or partially diffused characteristics of the reference source. In another embodiment, the crown is made of glass with a coating applied to the external side to achieve diffused or partially diffused characteristics of the reference source. In another embodiment, the external side of a glass crown is made rough in order to improve its diffusive characteristic and to facilitate cleaning of the internal, smooth surface of the crown.

In another aspect, if an instrument produces a target image, the geometry of the external reflector can include a multiplicity of smaller reflectors (ribs) which will allow the instrument to achieve sufficient reflection and yet will not completely block the field of view of the instrument. In case of an imaging instrument, this can also minimize the obstruction of peripheral vision of the optical instrument. In one embodiment, the crown is formed with a plurality of side reflectors. In another embodiment, the teeth of the crown are rectangular or rounded rectangular. In some embodiments, the crown has multiple teeth with crenellations selected in view of both the ability of the crown to diffuse light in the direction of the window and the possibility of restoring the peripheral view to a substantially complete state.

In another aspect, the single light source or each of the plurality of light sources emits electromagnetic radiation at a controlled frequency of modulation. The detector is accordingly adapted to detect radiation at the same controlled frequency of modulation in order to differentiate the measured light from the ambient radiation.

In one embodiment, the optical instrument uses the same light detector to detect window contamination as the normal incident radiation from a target object being measured. In another embodiment, the optical instrument is equipped with a dedicated light detector detecting light reflected by the crown only.

In another aspect, the optical instrument is equipped with a microcontroller or an Application Specific Integrated Circuit (ASIC) adapted to control the light source or sources and to process signals from the light detector. In one embodiment, the controller or ASIC is further equipped with a programmable memory. In one embodiment, the programmable memory stores a plurality of constants related to spectral qualities of various parts of the optical instrument. In another embodiment, the programmable memory additionally stores an algorithm for detecting the presence or absence of a contaminant in a certain position on a window based on radiation signals detected by the light detector at each wavelength of light emitted by one or several light sources.

In another embodiment, an optical instrument having a window is equipped with a light source not restricted to transmitting electromagnetic radiation at a controlled wavelength, a crown having a curvature and surface characteristics consistent with one of the embodiments discussed above, and a light detector disposed on the opposite side of the window relative to the crown. The crown spreads the light emitted by the light source uniformly across the entire surface of the window and the light detector detects the amount of radiation transmitted through the window. In one embodiment, a controller coupled to the light source and to the light detector is programmed to detect the presence or absence of foreign particles on the window by comparing the amount of radiation emitted by the light source to the amount of radiation collected by the light detector. In particular, the controller may calculate a ratio of the two compared quantities and compare the ratio to a predefined threshold level for a selected part of the window surface.

In some embodiments of the system and method for detecting contamination described herein, a ratio measurement at two selected wavebands replaces the absolute intensity measurement. In other words, these embodiments use a spectroscopic measurement at two predetermined spectral regions selected for the maximum sensitivity to a particular type of contamination. Because a system using multiple wavebands uses a relative change in the transmissivity of the window for two or more spectral regions rather than relying on an absolute measurement of intensity, the system may minimize the impact of the following factors: mechanical movement of the source/detector combination; optical misalignment between the source and the detector; contamination of the source and external reflectors; and temperature coefficients and drifts of the source and detector.

In general, the method and apparatus consistent with the teachings of the present disclosure may be applied in infrared (IR) thermometers, flame detection instruments, gas detection instruments, monitoring of marine beacons, machine vision applications, industrial robotics, security vision systems, nigh vision devices, automotive applications, detection of biofilms on underwater instrumentation, and a variety of other applications. The wavelength and intensity values of each light source may be tunable in order to make the optical instrument most optimal for each specific operating condition.

In some implementations, a multi-waveband contamination detection system may use a UV LED operating at 360 nm and a visible LED operating at wavelength of 650 nm, or, as another example, a combination of an LED operating at visible spectral region and a near-infrared LED operating at wavelengths of approximately 1550 nm. Similarly, the intensity of each light source may also be tunable because the thickness of the window (or optical front lens) may vary significantly and also because certain applications, such as those associated with extremely dusty or dark conditions, may require higher power in order for the light to reach the crown and travel back to the detector in a diffused form.

DETAILED DESCRIPTION OF THE DRAWINGS

DETAILED DESCRIPTION

Figure 1:
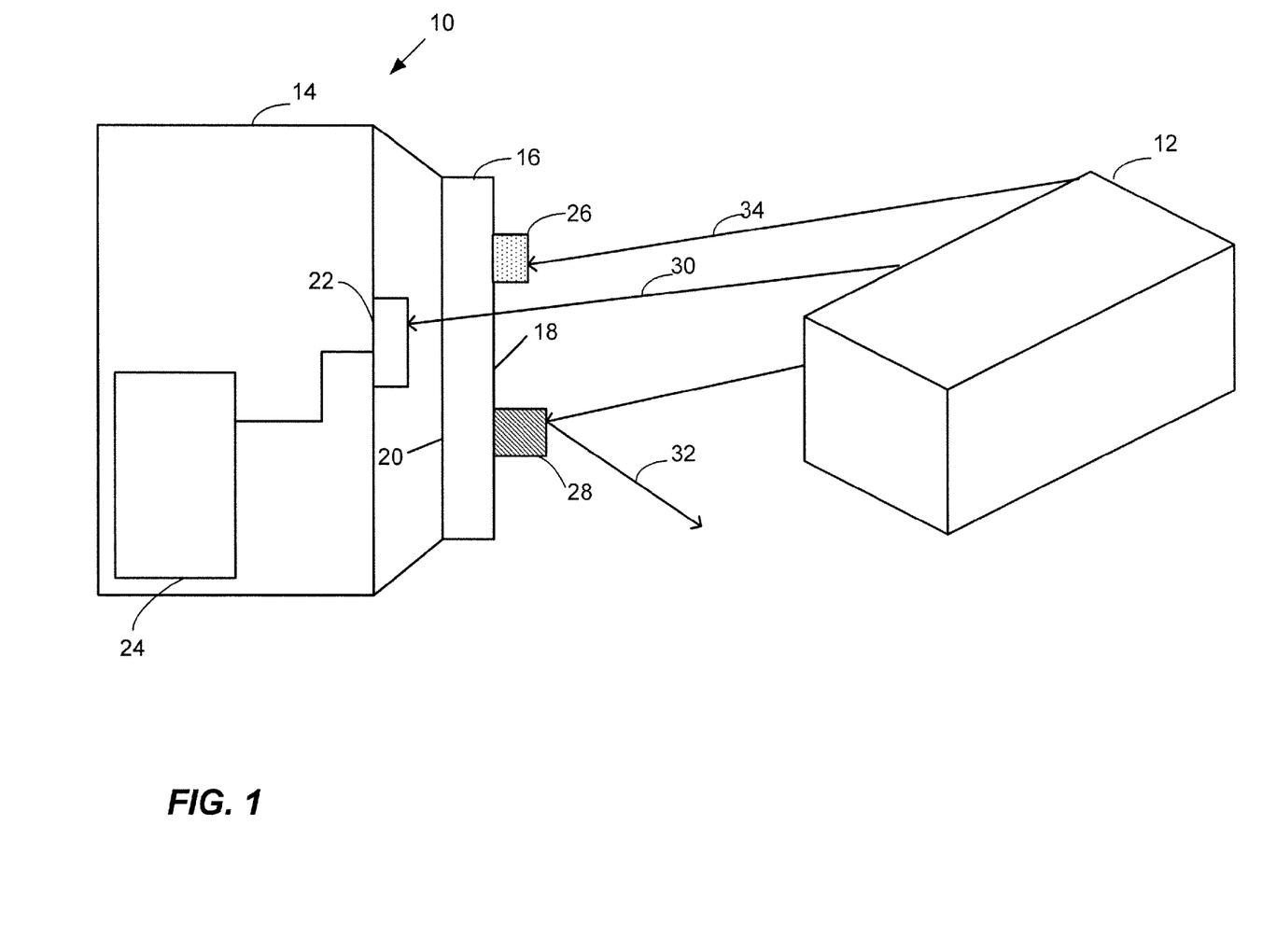
FIG. 1 is a schematic representation of an optical instrument with a contaminated window measuring radiation emanating from a target object.

FIG. 1 is a schematic representation of an optical instrument or measuring device 10 remotely measuring the temperature of a body 12. The device 10 contains a housing 14, a transmissive pane or window 16 with a first (external) side 18 and a second (internal) side 20, and a light detector 22. Additionally, a controller 24 may be disposed inside the housing 14. In operation, the optical measuring device 10 detects electromagnetic radiation emanating from the body 12. More specifically, the detector 22 may generate a voltage signal indicative of the intensity of incident electromagnetic radiation and propagate the voltage signal to a processing unit such as the controller 24. However, the controller may be disposed outside the housing 14 and be communicatively coupled to the device 10 in a conventional way, such as via a copper wire, for example.

Under certain operating conditions, dust, debris, and other foreign particles may accumulate on the external side 18 of the window 16. As illustrated in FIG. 1, foreign particles 26 and 28 may appear in the path of incident electromagnetic radiation and may absorb or deflect some or all of the radiation traveling in the direction of the detector 22. For example, a radiation beam 30 may pass unobstructed through the window 16 and reach the detector 22. Meanwhile, the foreign particle 28 may reflect a ray 32 and direct the ray 32 away from the surface 18, thus preventing the detector 22 from registering a voltage corresponding to the intensity of the ray 32. On the hand, the particle 26 may absorb a ray 34, similarly preventing the ray 34 from reaching the detector 22. One of ordinary skill in the art will also appreciate that a contaminant may also allow electromagnetic radiation to pass through the contaminant but may reduce the intensity of the radiation thus affecting the voltage produced by the detector 22 and, ultimately, the readout of the optical device 10. In short, contaminants of various types may accumulate on the side 18 of the window 16 and interfere with the output of the optical device 10. Thus, the device 10 requires an efficient, reliable and preferably inexpensive means of detecting contamination of the window 16.

Figure 2:
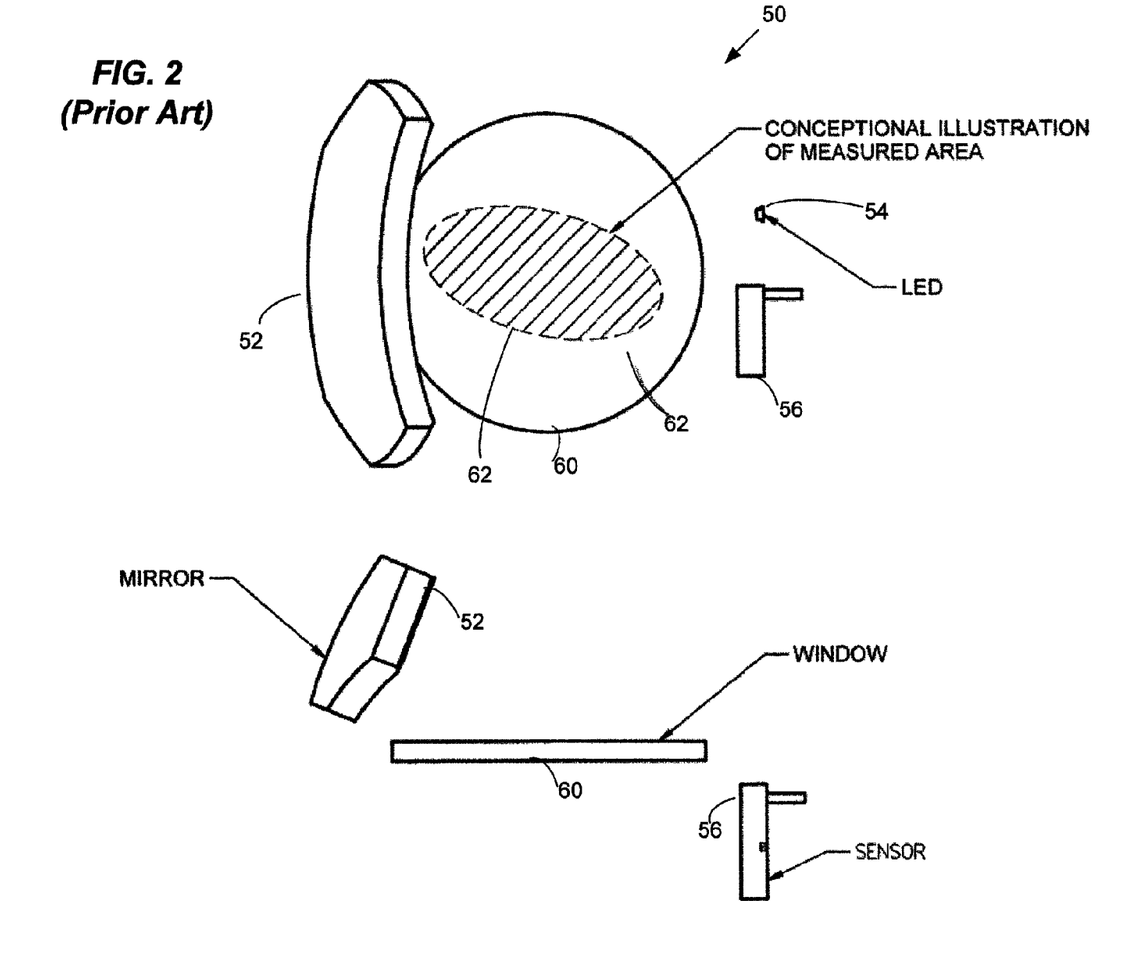
FIG. 2 illustrates a dirty window detector known in the art which is limited to covering only part of the window surface.

Referring to FIG. 2, a system 50 known in the art includes a reflective element 52, an LED 54, and a sensor 56. In operation, the LED 54 directs light through a window 60 toward the reflective element 52. The light reflected off the reflective element 52 passes through the window 60 and may be detected by the sensor 56, depending on the level of contamination of the window 60. The system 50 may thus attempt to detect contamination in a coverage area 62. As illustrated in FIG. 2, the coverage area 62 does not correspond to the entire surface area of the window 60. In other words, area 64 is outside the range of vision of the system 50 and thus any contamination accumulating in the area 64 cannot be detected.

Figure 3:
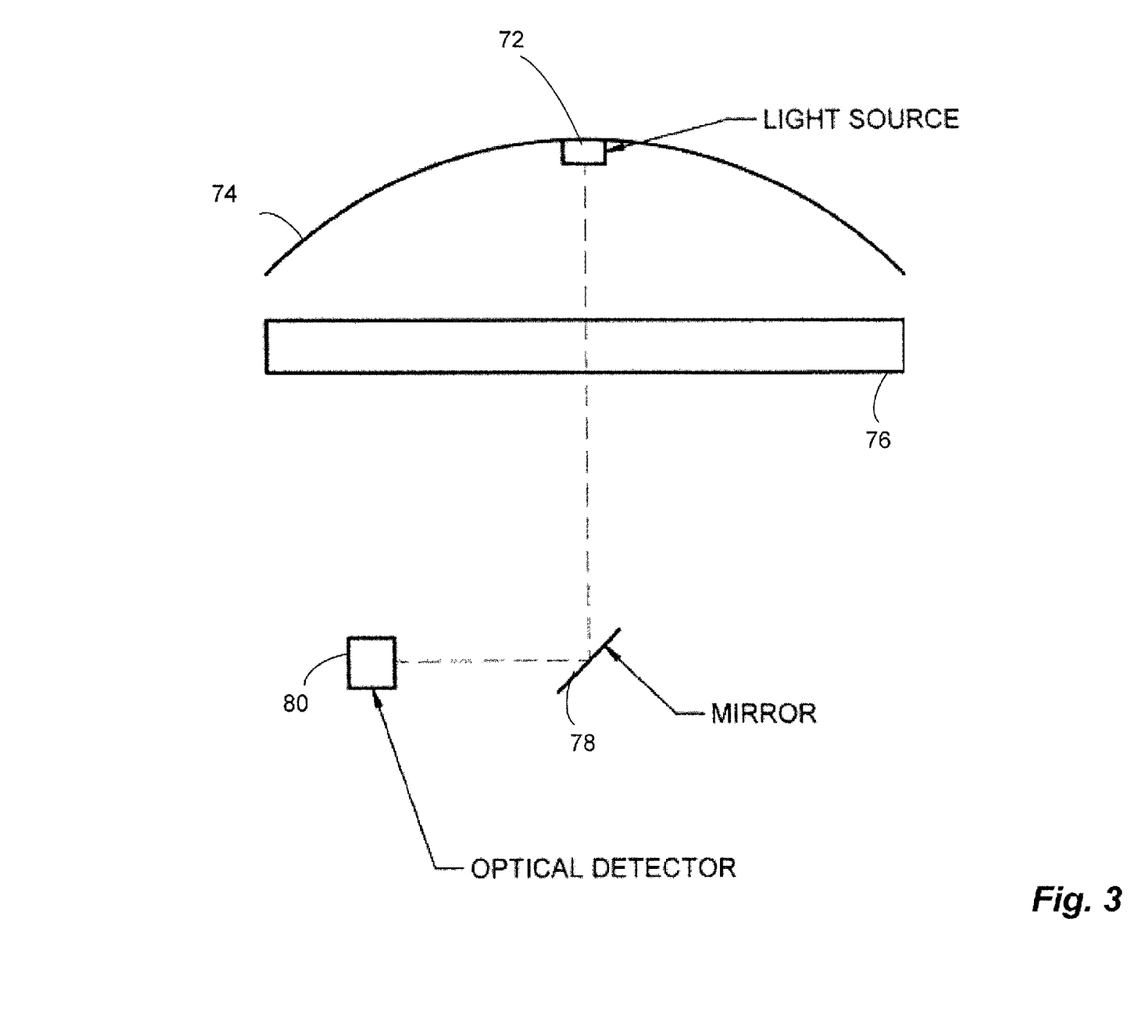
FIG. 3 illustrates another type of a dirty window detector known in the art which relies on a light source suspended in front of the window.

On the other hand, FIG. 3 schematically illustrates another known approach to the problem of detecting window contamination. A system 70 has a light source 72 suspended by a bridge 74 over a window 76. The window 76 is part of an optical device (not shown) detecting electromagnetic radiation emanating from a target object disposed on the same side as the light source 72 relative to the window 76. Thus, the light source 72 is placed directly in the path of incident radiation and, therefore, obstructs some of the radiation measured by the optical device. Moreover, the bridge 74 presents another obstacle for incident radiation and thus introduces another source of uncertainty.

In operation, the system 70 attempts to detect contamination on the window 76 by directing light from the light source 72 through the window 76 to an optical detector 80 via a mirror 78. However, one will additionally recognize that because the light source 72 is disposed outside the optical device which includes the window 76, the light source 72 is equally susceptible to contamination.

Figure 4:
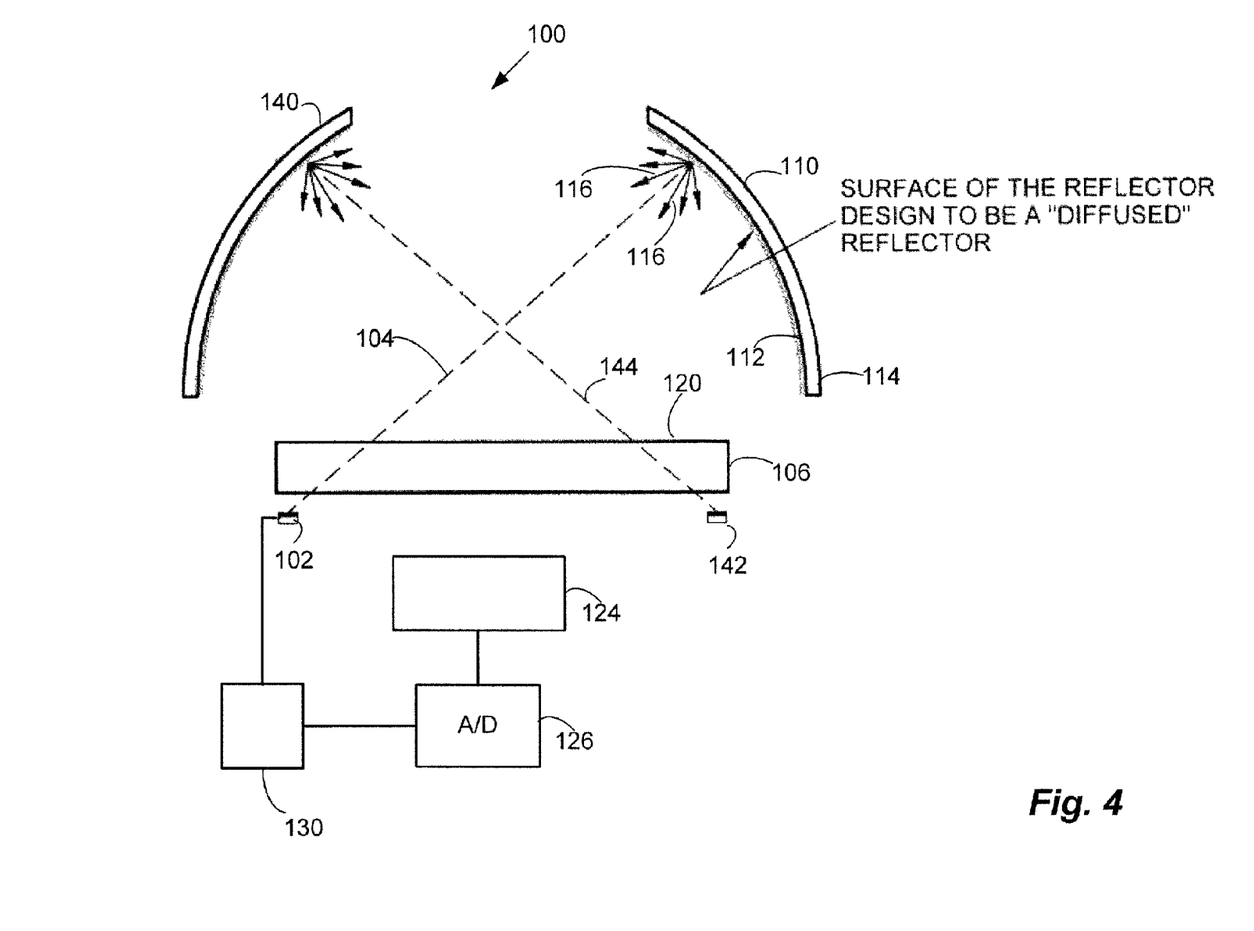
FIG. 4 illustrates a window and a fragment of a concave wall of a crown used in an optical window contamination monitor implemented according to the teachings of the present disclosure.

FIG. 4 illustrates a window contamination detector 100 corresponding to one of the embodiments of the present disclosure. In operation, an emitter 102 directs a beam of electromagnetic radiation 104 through a window 106 toward a first diffusing reflector 110. The diffusing reflector 110 has an inner surface 112 and an outer surface 114. In the embodiment depicted in FIG. 4, the inner surface 112 is adapted to be diffusive with respect to incident radiation. Thus, the beam of electromagnetic radiation 104 is not reflected off the surface 112 in a focused manner. Instead, the beam 104 is scattered, or diffused, upon coming into contact with the inner surface. One of ordinary skill in the art will appreciate that while the beam 104, once scattered, is shown as a plurality of beams 116, FIG. 4 illustrates the phenomenon only schematically and does not attempt to accurately represent the actual physical process of light scattering or diffusive reflection.

The diffusing reflector 110 may be manufactured from a relatively durable material such as glass or plastic. In many applications, and particularly in high temperature environments, it may be preferable to manufacture the reflector 110 from a metal or alloy. Depending on the material selected for the reflector 110, the inner surface 112 may be sandblasted, coated, painted white, or otherwise machined to provide sufficient diffusion of light. It will be appreciated that many of the other known methods of manufacturing parts having diffusive surfaces can be equally suitable for the diffusing reflector 110. Similarly, the body of the diffusing reflector 110 may be inexpensively manufactured from a number of other materials in addition to metal, glass, or plastic.

The diffusing reflector 110 is bent, formed or machined in such as a way as to produce a curvature suitable for spreading the diffused light 116 over an outer surface 120 of the window 106. The radius of the curvature may vary in different implementations and in view of such geometric factors as the distance between the outer edge of the window 106 and the diffusing reflector 110 and the surface area of the window 106. Moreover, several diffusing reflectors having different curvatures may be equally compatible with the same window 106 if, for example, the diffusing reflector is placed closer to or farther from the outer edge of the window 106.

Referring again to FIG. 4, the diffused light 116 passes through the window 106 and is collected by a detector 124. The detector 124 may be any photoelectric detector capable of producing a voltage or current signal indicative of the intensity of the incident radiation. Further, the detector 124 may consist of an array of optical sensors producing a set of signals corresponding to various regions of the window 120. One of ordinary skill in the art will recognize that various detector arrangements are possible and that the window contamination detector 100 may be implemented using one or several detectors 124 with one or more photoelectric elements.

An A/D converter 126 communicatively coupled to the detector 124 may then convert the analog radiation signal to a digital signal and forward the digital signal to a controller 130. The controller 130 may process the signal and determine whether contamination is present on the surface 120 of the window 106. The controller 130 may also provide drive signals to the emitter 102 or to multiple emitters, depending on the chosen configuration. The controller 130 may, at some stage of operation, compare the amount of the detected radiation corresponding to a certain region of the window 106 to the amount of radiation 104 emitted by the emitter 102. Because the radiation 104 is scattered across a relatively large area, the controller 130 may accordingly compare the radiation 104 to a significantly smaller value corresponding to the amount of radiation an uncontaminated region of the window 106 should allow. The controller 130 may thus generate a map or a list of regions of the window 106 where the amount of radiation penetrating the window 106 falls below a predefined threshold. Alternatively or additionally, the controller 130 may compare the amount of detected radiation at each region to the amounts associated with other regions in order to determine relative contamination of each region of the window 106.

It will be appreciated that the detector 124 may be the same detector used by the optical device 10 for measuring radiation of a target object, such as, for example, an infrared detector used in non-contact temperature measurements. Similarly, neither the A/D converter 126 nor the controller 130 need be dedicated devices used exclusively for window contamination monitoring. In other words, the window contamination detector 100 may be inexpensively implemented without any dedicated optical detection circuitry and may effectively steal or scavenge some of the processing power of a controller servicing the optical device 10.

Referring again to FIG. 4, the window contamination detector 100 may include a second diffusive reflector 140 and a second emitter 142. The second diffusive reflector 140 may be the same in shape in composition as the diffusive reflector 110. The second emitter 142 is positioned so as to emit a beam of electromagnetic radiation 144 in the direction of the diffusive reflector 140. As illustrated in FIG. 4, the emitters 102 and 142 may be positioned diagonally across from the respective diffusive reflectors 110 and 140 so that the maximum amount of radiation emitted from the emitters 102 and 142 is diffused over the surface 120. In an embodiment which involves two diffusive reflectors and two emitters, the diffusive reflectors 110 and 140 may be placed opposite each other along the diameter of the window 106. Analogously, if the window 106 is square or rectangular, the diffusive reflectors 110 and 140 may be placed at the opposite sides of the window 106 so that each diffusive reflector preferably spreads equal amount of radiation across the surface 120 of the window 106. However, one of ordinary skill in the art will appreciate that other, non-symmetrical arrangements may also be possible.

According to one possible embodiment, the emitters are activated in a "rapid fire" mode. For example, three emitters such 102 or 142 may be placed equidistantly from each other along the circumference of the window 106. In operation, the first emitter may emit a radiation signal for a predetermined amount of time followed by a second emitter emitting a radiation signal of the same intensity for the same amount of time, and finally followed by third emitter doing the same. This solution may be helpful in minimizing the interference between the sources. It may also provide some level of redundancy in case one or more emitters should fail.

It is also contemplated that the selection of an angle at which the emitter 102 or 142 may direct a radiation signal through the window 106 and toward the diffusive reflectors 110 or 140 may also vary according to the properties of the optical device 10. In one aspect, the angle may be selected in view of the thickness of the window 106. However, it will be noted that other factors, such as the geometry of the diffusive reflectors 110 or 140, may also be taken into consideration.

In another embodiment, the emitters 102 and 142 may be positioned on the same side of the window 106 as the diffusive reflectors 110 and 140. By properly selecting the geometric parameters of the reflectors 110 and 140, it is possible to provide substantially the same coverage of the window 106 by diffusely reflected light. This type of emitter positioning may also allow the window contamination detector 100 to transmit energy at lower power because the radiation emitted by the emitters 102 and 142 need not pass through the window 106 before reaching the diffusive reflectors 110 and 140. However, one of ordinary skill in the art will note that by placing the emitters behind the window 106 and thus inside the housing of the optical device, one may protect the emitters 102 and 142 from accumulating contaminants, as well as from other environmental factors.

Figure 5:
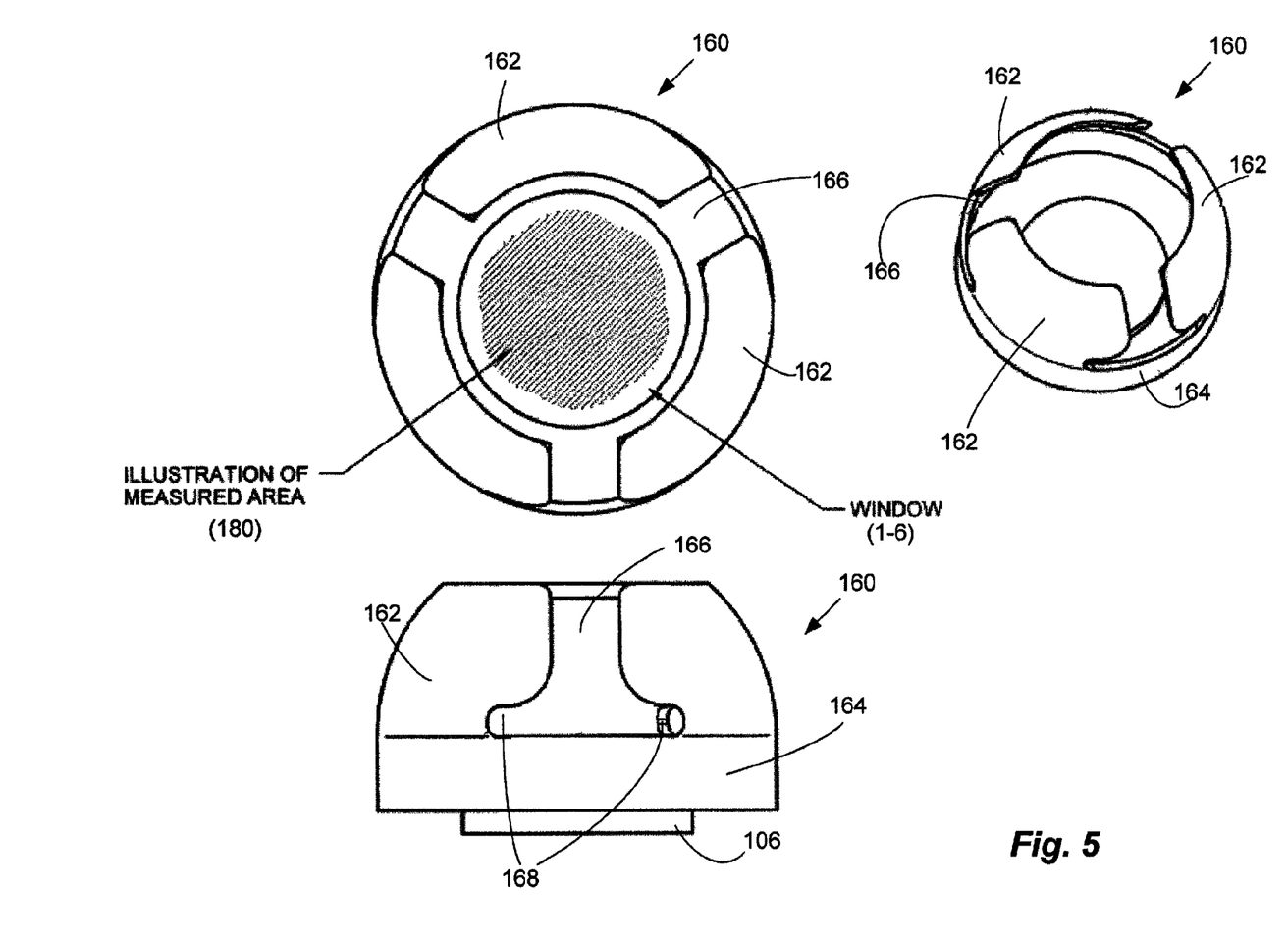
FIG. 5 illustrates several perspectives of a crown consistent with one of the embodiments.

In accordance with some contemplated embodiments, a plurality of diffusive reflectors similar to 110 and 140 form an integral unit in shape of a crown. The crown may be adapted to surround the circumference of a circular window of an optical device. Referring now to FIG. 5, a crown 160 may have three diffusive reflectors 162 placed on a support 164 at the same distance relative to each other. Accordingly, the openings 166 between each respective pair of diffusive reflectors 162 have the same spatial dimensions. The support 164 may not have a significant curvature and may instead be implemented as a solid strip of metal, plastic, or glass forming a ring, with walls of the ring forming a perpendicular line relative to the surface of the window 106. Of course, the support 164 may be made of the same material as the reflectors 162 and it is further contemplated that the entire crown 160 may be cast or molded as a single integral unit.

Additionally, the crown 160 may have apertures 168 between each of the corners of a diffusive reflector 162 and the support 164. The apertures 168 may effectively widen each opening 166 on the side proximal to the support 164. The openings 166 and the apertures 168 may significantly improve the peripheral vision of an optical device on which the crown 160 is mounted. Because of the wide range of applications in which the window contamination detector 100 and, in particular, the crown 160 may be used, it is desirable to minimize the impact of window contamination detection on other aspects of operation of the corresponding optical instrument. Thus, while certain optical devices such as non-contact infrared optical thermometers may measure electromagnetic radiation from target objects located directly in front of the optical device, other instruments such as robotic vision systems may be equally concerned with objects anywhere in the hemispherical field of vision.

The crown 160 is capable of illuminating the entire surface of the window 106 by diffusing light emitted by one or more light sources located on the other side of the window 106 relative to the crown 160. The number of light sources or emitters may be the same as the number of diffusive reflectors in the crown. For example, there may be an emitter such as 102 or 142 pointed at each of the diffusive reflectors 162. In FIG. 5, an area 180 is depicted as covering substantially the entire working area of the window 106. Referring back to FIG. 2, the area 180 is equal to areas 62 and 64 combined assuming the windows 106 and 60 have the same shape and surface area. Moreover, because the support 164 has a radius exceeding that of the window 106 (or a working area of the window 106), no part of the crown 160 obscures light incident on the window 106 at the right angle. Preferably, the curvature of the diffusive reflectors 162 is selected in view of both the circumference of the support 164 and the circumference of the window 106, and the difference between the circumferences of the outer and inner rims of the reflectors 162 does not exceed the difference in circumferences of the support 164 and window 106.

Figure 6:
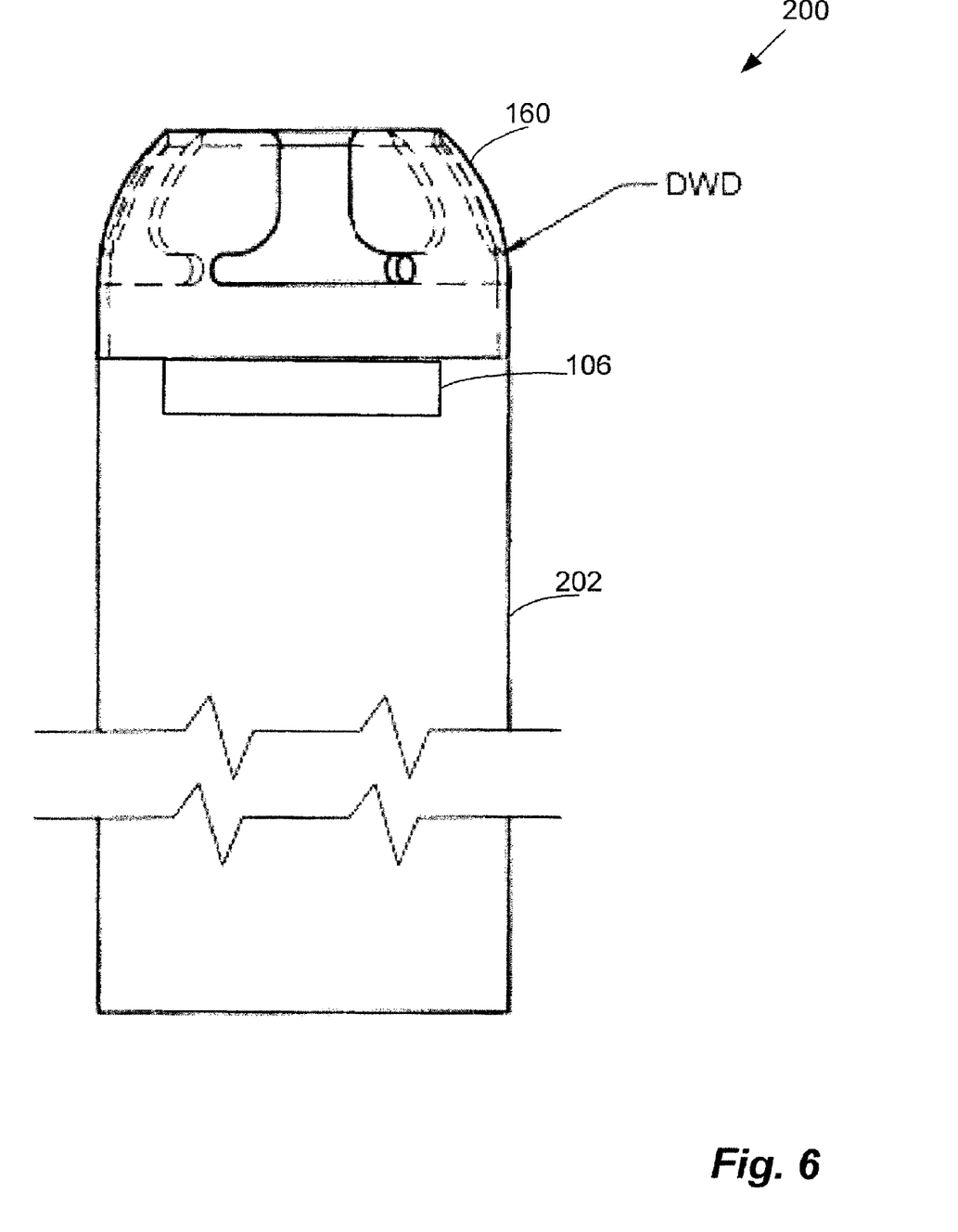
FIG. 6 illustrates one of the disclosed embodiments of a crown mounted on an optical device.

As illustrated in FIG. 6, a window contamination monitor 200 may include the crown 160 mounted on an optical device housing 202. The crown 160 may be attached to the housing 202 by any means known in the art, either in a permanent or removable fashion. It is contemplated that in certain applications, it may be desirable to be able to remove and attach the crown 160 as needed. To this end, the crown 160 may be provided with grooves or flutes for mating with the housing 202.

The monitor 200 may detect contamination of the window 106 by using emitters such as the emitter 102 or 142. As discussed above, the number of emitters may vary. In accordance with one approach, the number and positioning of emitters are selected in view of a particular crown configuration. For example, a crown with 12 diffusive reflectors may work well with a 4-emitter configuration so that each emitter covers a 90° sector of the circumference of the crown and directs light at the 3 reflectors facing the emitter most directly. In another embodiment, a single emitter may be used and periodically moved along the circumference of the window 106. It is also contemplated that an optical ring may be used in order to provide a uniform source of electromagnetic radiation along circumference of the window 106.

The window contamination detector 100 or 200 may improve the quality of detection by using measurements at multiple wavelengths of electromagnetic radiation. In particular, the window contamination detector 100 may generate a first electromagnetic radiation signal having a first wavelength and produce a first voltage reading at the detector 124. The window contamination detector 100 or 200 may then generate a second electromagnetic radiation signal having a second wavelength and produce a second voltage reading at the detector 124. The monitor may then use the first and second voltage readings in order to detect the presence or absence of foreign particles on the window 106.

In order to appreciate some of the advantages afforded by the multiwavelength approach, one may recall that the voltage produced by a photoelectric detector in response to incident light depends on a plurality of factors, including the spectral quantities of the medium and the detector. In general, the relationship between the transmissivity $\tau_w$ of a certain medium such as a window of an optical device with respect to a certain wavelength w, and voltage output by the detector, $V_{out}^{\lambda_w}$, is given by:

$$V_{out}^{\lambda_w} = R_{\lambda_w}^D * \psi * N_{\lambda_w} * \tau_w$$

where $R_{\lambda_w}^D$ is the responsivity of the detector to light at the wavelength $\lambda w$, $\psi$ is the geometry of the field of vision of a detector, and $N_{\lambda_w}$ is the radiance of the light with wavelength w.

In many conditions where optical instrumentation is used, and especially in industrial applications, some of the factors determining $V_{out}^{\lambda_w}$ unpredictably and rapidly vary with time, thus introducing uncertainties into the calculations and ultimately into the process of detecting window contamination. In particular, $\psi$ may change due to a sudden movement, shock and vibration of the optical device 10. An operator may inadvertently push the optical instrument and create a barely perceptible change in $\psi$ which may nevertheless result a wrong value of $V_{out}^{\lambda_w}$. Meanwhile, the responsivity factor $R_{\lambda_w}^D$ has a dependency on age, and as the detector gets older, the output may at some point start drifting.

It is also important to note that most materials and substances do not exhibit the same transmissivity with respect to different wavelengths of radiation. In the optical range, the transmissivity of most liquids with respect to near-infrared light is very low while blue light may go through the same liquid relatively well. Conversely, small dust, mist, or other scattered particles poorly transmit blue light while displaying high transmissivity with respect to infrared or near-infrared. Analogously, there are substances with low green transmissivity and relatively high transmissivity of red or blue colors.

The window contamination detector 100 may use two optical signals, such as green and red light beams, in order to arrive at a much more accurate detection of potential window contamination. One of ordinary skill in the art will recognize that a multitude of different optical signals could be used, such as, for example, UV and near IR. As follows from the discussion above relative to green and red light beams, the relationship between the tranmissivity of the medium and the voltages for red light is given by $$V_{out}^{\lambda_R} = R_{\lambda_R}^D * \psi * N_{\lambda_R} * \tau_R$$

and by $$V_{out}^{\lambda_G} = R_{\lambda_G}^D * \psi * N_{\lambda_G} * \tau_G$$

for green light.

Thus, the ratio of $V_{out}^{\lambda_R}$ to $V_{out}^{\lambda_G}$ can be expressed as $(R_{\lambda_R}^D * \psi * N_{\lambda_R} * \tau_R)/(R_{\lambda_G}^D * \psi * N_{\lambda_G} * \tau_G)$. However, if a green light measurement and a red light measurement are performed in quick succession (milliseconds) at the same location, the geometric factor $\psi$ is unlikely to change significantly and can be safely factored out. Further, the ratio of radiances $N_{\lambda_R}/N_{\lambda_G}$ may be assumed to stay constant. Still further, the responsivity of the detector to red light and green light is likely to change at the same rate. Thus, the ratio of responsivities $R_{\lambda_R}^D/R_{\lambda_G}^D$ may be also assumed to stay constant. The ratio $V_{out}^{\lambda_R}/V_{out}^{\lambda_G}$ is therefore reduced to the ratio of transmissivity at green and red wavelengths corrected by a constant:

$$V_{out}^{\lambda_R}/V_{out}^{\lambda_G} = K * \tau_R/\tau_G$$

The window contamination detector 100 may determine the presence or absence of contamination, as well as the extent of contamination, from the ratio of the voltages output by the detector 124 for each of the green and red light beams. One of ordinary skill in the art will further appreciate that other selections of wavelengths are possible. For example, in certain conditions it may be preferable to use blue and yellow light beams and in other conditions it may be prudent to select blue and red, or UV LED and near IR LED. It is contemplated that the selection of wavelengths or colors should be made in view of the operating conditions in order to maximize the voltage ratio. Thus, it may be prudent to use radiation signals in the infrared or near-infrared part of the optical spectrum if most of the contamination is expected to come from grease because grease patches significantly attenuate infrared or near-infrared radiation while offering better transition at visible light.

In some embodiments, the constant associated with ratio of $N_{\lambda_R}$ to $N_{\lambda_G}$ and $R_{\lambda_R}^D/R_{\lambda_G}^D$ may be similarly ignored. It is contemplated that the window contamination monitor 100 may produce a set of values associated with the normal, or clean state of the window so that all subsequent measurements may be compared to these benchmark values.

Furthermore, the amount energy reflected from the internal (clean) part of the window can be factored out. In another embodiment, the voltages $V_{out}^{\lambda_R}$ and $V_{out}^{\lambda_G}$ may be programmed in the controller 130 or stored in a memory (not shown) coupled to the controller 130. Further, the thickness of the window 106, the chemical composition of the window 106, and other factors may have impact on the voltages $V_{out}^{\lambda_R}$ and $V_{out}^{\lambda_G}$. The window contamination detector 100 may store a plurality of possible configurations in the form of a table. Alternatively, the controller 130 may be adapted to communicate with an input means (not shown) to accept window and environment specific parameters from an operator. In some other embodiments, the window contamination detector 100 may be specifically configured for a certain environment and may be manufactured as an integral part of the optical device 10. For example, an optical system intended for underwater use may be provided with the window contamination monitor 100 which is specifically adapted to generate blue and green radiation beams at an intensity selected in view of the thickness and composition of the window 106.

In some embodiments, the emitters 102 or 142 are bicolor or tricolor Light Emitting Diodes (LEDs). Bi- or tricolor LEDs may be voltage dependent, so that the controller 130 or a dedicated control circuit could select between a first wavelength, a second wavelength, and a combination thereof by applying a different voltage across the LED. However, it is also possible to use two or more single-color LEDs, each LED associated with a different wavelength. One of ordinary skill in the art will recognize that any means of generating separate radiation signals with at least two distinct wavelengths may be used. As another example, it is possible to provide a single source of white light and provide a means of sequentially applying filters to the light source. In other words, the source of electromagnetic radiation may simultaneously emit "mixed" radiation signals containing multiple wavelengths and a dedicated auxiliary device may be adapted to selectively block and unblock signals associated with the selected wavelengths. To continue with this example, a chopper could cyclically apply green and red optical filters to a source of white light in order to alternate between green and red wavelengths. However, it will be appreciated that other approaches are equally possible and that in general, any known means of generating electromagnetic radiation signals having a single controlled wavelength may be used.

In some of the embodiments, the window contamination detector 100 or 200 could additionally modulate the signals from the emitters 102 or 142 in order to separate these signals from the ambient light sources. One of ordinary skill in the art will appreciate that modulation may be particularly relevant in the environments where electromagnetic radiation of the same or proximate wavelength as the signals from the emitter 102 or 142 may be present. Moreover, the electromagnetic signals from the target object being measured, detected, or otherwise processed by the optical device 10 may also contain radiation having the same wavelength as the signal from the emitters 102 and 142. It is therefore desirable to provide the window contamination detector 100 with an efficient means of separating the relevant signals from the ambient radiation.

In order to provide modulation, the window contamination detector 100 or 200 can use an electronic modulation of the LED source. Thus, as one skilled in the art will easily recognize, each period of operation of the modulating device will have a "low" interval during which substantially all of the radiation emitted from the emitter 102 or 142 propagates in the direction of the diffusive reflectors 110 or 140 and a "high" interval during which substantially all of the radiation emitted from the emitter 102 or 142 is blocked. The detector 124 will accordingly register incident radiation characterized by two distinct intervals alternating at the frequency of operation of the modulating device. The controller 130 may then subtract the level of radiation detected during low intervals from the level of radiation detected during high intervals and thus counteract the effects of the ambient noise. In addition to carrying out relevant calculations, the controller 130 may provide a synchronization signal for demodulation circuitry.

Figure 7:
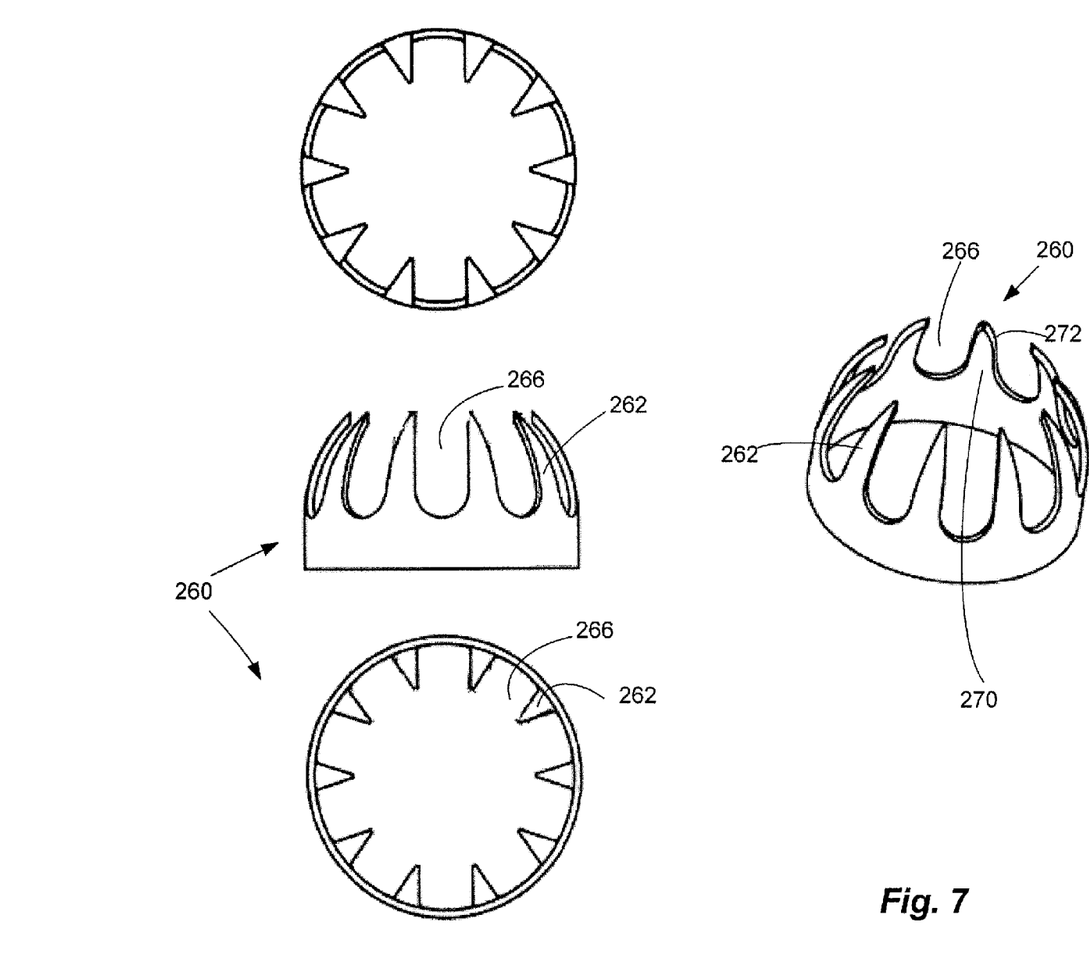
FIG. 7 illustrates a disclosed embodiment of a crown with tapered teeth.

As mentioned above, the same controller 130 or a separate computing unit may also apply one of the algorithms known in the art to the data collected by the optical device 10 in order to restore the image partially obscured by the crown 160. One of ordinary skill in the art will recognize, however, that the view may not be easily restored if the geometry of the crown blocks certain parts of the view. Thus, several alternative configurations of a crown are contemplated. Referring to FIG. 7, a crown 262 has a plurality of tapered teeth 262. Thus, the openings 266 between teeth 262, through which the optical device 10 may see some of the periphery, are made larger. Meanwhile, the teeth 262 provide a diffusively reflective surface either on the internal side 270 or, if the crown 260 is fully or partially transparent, on the external side 272. Similarly to the diffusive reflector 110, for example, each of the teeth 262 may have a curvature adapted to scatter an incident radiation beam over the surface of the window 106.

Figure 8:
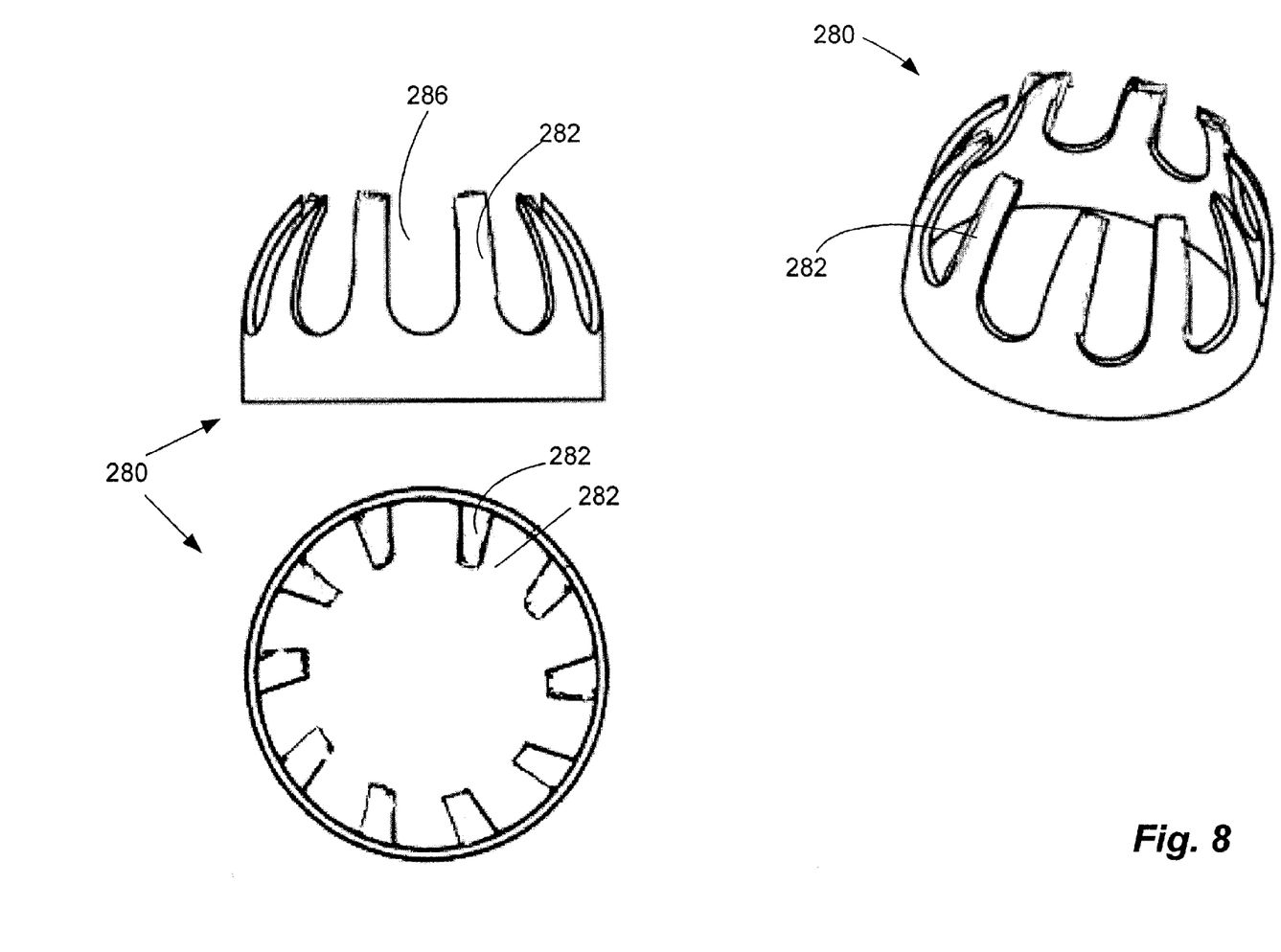
FIG. 8 illustrates a disclosed embodiment of a crown with rectangular teeth.

In another embodiment illustrated in FIG. 8, a crown 280 has teeth 282 of a substantially rectangular or rounded rectangular form. As part of a tradeoff with the embodiment illustrated in FIG. 7, the openings 286 between teeth 282 are smaller but the combined surface of diffusively reflective teeth 282 is increased. In general, one of ordinary skill in the art will appreciate that many other crown configurations are also possible and that the crowns 160, 260, and 280 are provided by way of example only.

Figure 9:
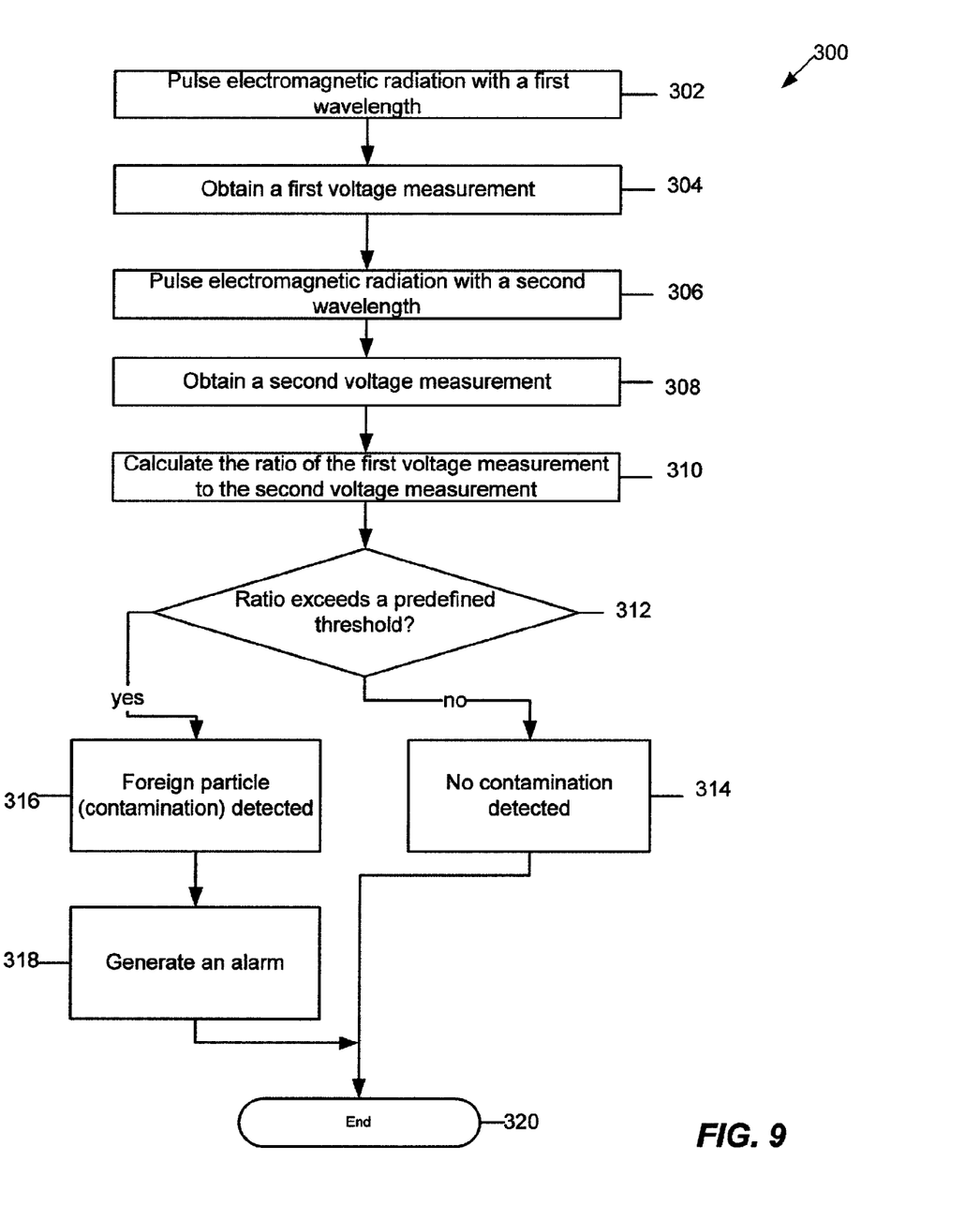
FIG. 9 is a flowchart illustrating an exemplary algorithm for detecting the presence or absence of contamination on a window of an optical device using electromagnetic radiation associated with two different wavelengths.

FIG. 9 illustrates an exemplary procedure 300 which may be implemented in any programming language such as C, C++, or Fortran, and executed by the controller 130. However, it will be noted that the procedure 300 may also be executed in a distributed manner, such as in part by the controller 130 and in part by a dedicated circuit driving the emitters 102 or 142, to take one example.

At a block 302, the procedure 300 may instruct the emitter 102 to generate a first radiation signal associated with the first wavelength. In a block 304, the procedure 300 may obtain a corresponding voltage signal from the photoelectric detector 124 via the A/D converter 126. The procedure 300 may, in the block 304, save a numeric representation of the voltage signal into a first variable.

In a block 306, the procedure may instruct the emitter 102 to generate a second radiation signal associated with the second wavelength. As discussed above, the emitter may be tunable and the procedure 300 may communicate an actual wavelength to the emitter in the block 306. Alternatively, the procedure 306 may simply activate the second separate emitter adapted to emit radiation at the second wavelength. In yet another embodiment, the procedure 300 may, in the block 306, generate a voltage signal which will cause a bi- or tri-color LED to emit a radiation signal having the desired wavelength.

A block 308 may be similar to the block 304. As part of this step, the procedure 300 may record the second voltage measurement and proceed to a block 310. In the block 310, the procedure 300 may calculate the ratio of the two voltages. The procedure 300 may optionally adjust the ratio by a constant associated with the difference in radiance and detector responsivity associated with the two colors, or wavelengths of the emitted radiation.

The procedure 300 may decide, in a block 312, whether a predefined threshold has been exceeded. In particular, the procedure may compare the obtained ratio to a benchmark or threshold value corresponding to transmission through an uncontaminated section of the window 106. The benchmark may be predefined and stored in the controller 130 as a constant. It is also contemplated that the benchmark value may be obtained automatically. For example, the controller 130 may calculate the benchmark value as part of a start-up procedure when the window 106 is known to be clean.

If the calculated ratio does not exceed the benchmark value, the procedure 300 may decide that the section of the window being processed is free of contamination. The procedure 300 may store the results of contamination monitoring in a volatile memory such as RAM and may, in a block 314, update the result of contamination checking. The procedure 300 may then proceed directly to an exit block 320.

If, on the other hand, the procedure 300 determines that the calculated voltage ratio exceeds the benchmark or threshold value, the procedure may update a different memory location at a block 316 or may simply record a different value in the memory location storing all of the results of contamination checking. Optionally, the procedure 300 may then generate an alarm in a block 318 in order to bring the result of the checking to an operator's attention.

Additionally, the measurements and calculations obtained by a multiwavelength window contamination detector 100 or 200 may also be used to adjust the optical reception of the optical device 10. More specifically, the results recorded in the blocks 314 and 316 of the procedure 300 may be used to generate a map of known contamination so that the optical device may make proper adjustments to the measurements until the window 106 is properly cleaned or replaced.

It should be noted that dust is one of the most common sources of particles in the atmosphere. Dust particles can range widely from less than about 100 microns in diameter to larger than 100 microns. These particles can include organic materials, carbon products, various mineral particles, oil droplets and even water droplets from the atmospheric moisture which can be randomly deposited on the surface of an optical window. Windows contaminated by the deposited dust attenuates optical radiation emitted by the targets (in case of radiometric measurements such as: infrared radiometry, flame detection etc.), and reduces the intensity and image contrast as a result of background light scattering for the imaging systems. Both reflective and transmissivity characteristics of the dust have strong dependency on the wavelength of observation.

In the proposed embodiments discussed above, the absolute transmissivity measurement at a single spectral bandwidth can be replaced with the measurement of differences in optical transmissivity at two selected spectral bandwidths. Furthermore depending on the specific environment (thus type of the dust contamination) these two spectral regions can be selected to achieve the highest sensitivity to the levels of the dust contamination.

This type of detection is based on a well established fact of dependencies between optical transmissivity of a window vs. wavelength of observation and the type of the window contamination. Furthermore, this detection allows establishing a very specific property, the window contamination, namely: "gray" attenuator vs. "spectrally selective attenuator." This represents critical information for a special class of instruments which are based on the ratio measurements. Specifically, this includes ratio Infrared radiometers (thermometers). These thermometers strongly rely on the change in spectral distribution of the target radiation to infer accurate temperature measurements. Using a "spectrally selective" window in front of this type of instrument will create a drastic error and render the instrument unusable. Therefore, in the case of ratio based instruments, the proposed embodiments will not only detect the level of contamination, but it also will qualify the window for applicability for ratio based measurements.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

What is claimed is:

1. A foreign-particle detection system for use with an optical instrument having a transmissive window with a first side and a second side, the system comprising:
    a radiation source to emit a radiation signal;
    a diffusing reflector to diffusively spread the radiation signal emitted by the radiation source over the first side of the transmissive window, the diffusing reflector positioned relative to the transmissive window to not obscure light incident on the transmissive window at a right angle to the transmissive window;
    a radiation detector to detect, at the second side of the transmissive window, the diffusively spread radiation signal transmitted by the transmissive window, and to generate a detected radiation signal based on the detected diffusively spread radiation signal; and
    a computation module communicatively coupled to the radiation detector to detect a presence of foreign particles on at least one of the first side or the second side of the transmissive window based on at least the detected radiation signal.

2. The system of claim 1, wherein computation module includes a controller further coupled to the radiation source to control the radiation signal; and
    wherein the computation module detects the presence of foreign particles based on a first value of a parameter associated with the emitted radiation signal and a second value of the parameter associated with the detected radiation signal.

3. The system of claim 2, wherein the parameter is intensity of radiation.

4. The system of claim 1, further comprising:
    an analog-to-digital converter to convert the detected diffusively spread radiation signal to a digital signal for use by the computation module.

5. The system of claim 1, wherein the radiation signal includes a focused beam of radiation incident on the second side of the transmissive window that passes through the transmissive window prior to impinging upon the diffusing reflector.

6. The system of claim 1, wherein the diffusing reflector has a concave substantially transparent wall having an inner surface facing the transmissive window and an outer surface; and
    wherein the inner surface is free of diffusive coating and the outer surface includes a diffusive coating.

7. The system of claim 1 wherein the radiation detector is associated with both the foreign-particle detection system and with a primary function of the optical instrument.

8. The system of claim 1, wherein the radiation source is a ring illuminator aligned with a perimeter of the transmissive window and adapted to emit radiation of at least two distinct wavelengths.

9. The system of claim 1, wherein the radiation source includes a plurality of emitters;
    wherein a first one of the plurality of emitters emits radiation having a first wavelength that produces a first value of the detected radiation signal;
    wherein a second one of the plurality of emitters emits radiation having a second wavelength that produces a second value of the detected radiation signal; and
    wherein the computation module uses the first value of the detected radiation signal and the second value of the detected radiation signal to detect the presence of foreign particles.

10. The system of claim 9, wherein the first one of the plurality of emitters emits green light and the second one of the plurality of emitters emits red light.

11. The system of claim 1, wherein the diffusing reflector has an inner surface facing the transmissive window, wherein the inner surface has a curvature towards the transmissive window suitable to diffusively spread the radiation signal emitted by the radiation source over the first side of the transmissive window.

12. A foreign-particle detection system for use with an optical instrument having a transmissive window with a first side and a second side, the system comprising:
    a radiation source to emit a radiation signal;
    a diffusing reflector to diffusively spread the radiation signal emitted by the radiation source over the first side of the transmissive window;
    a radiation detector to detect, at the second side of the transmissive window, the diffusively spread radiation signal transmitted by the transmissive window, and to generate a detected radiation signal based on the detected diffusively spread radiation signal; and
    a computation module communicatively coupled to the radiation detector to detect a presence of foreign particles on at least one of the first side or the second side of the transmissive window based on at least the detected radiation signal
    wherein the radiation source includes a plurality of emitters and wherein the system comprises a plurality of diffusing reflectors including the diffusive reflector;
    wherein each of the plurality of emitters directs a beam of radiation at a respective one of the plurality of diffusing reflectors.

13. The system of claim 12, wherein the plurality of emitters and the plurality of diffusing reflectors are positioned at regular intervals along a perimeter of the transmissive window; and
    wherein each of the plurality of emitters directs the respective beam diagonally across the perimeter so that the beam impinges the one of the plurality of diffusing reflectors farthest removed from the emitter.

14. The system of claim 12, wherein the plurality of diffusing reflectors define an integral unit shaped substantially as a concave crown having a plurality of openings between pairs of adjacent diffusing reflectors;
    wherein the plurality of openings increases a range of peripheral vision of the optical instrument.

15. The system of claim 14, wherein the crown further has a plurality of apertures, each aperture extending a respective one of the plurality of openings near the transmissive window to further increase the range of peripheral vision of the optical instrument.

16. The system of claim 14, wherein each of the plurality of diffusing reflectors is tapered at an end distal to the transmissive window.

17. The system of claim 14, wherein each of the plurality of diffusing reflectors is shaped substantially as a triangle with a base parallel to a surface of the transmissive window.

18. A method of automatically detecting foreign particles on at least one of a first surface or a second surface of a transmissive window of an optical instrument, comprising:
directing a first beam of electromagnetic energy at a diffusing reflector;
wherein the diffusing reflector spreads impinging radiation over the first surface of the transmissive window to produce a diffused radiation signal, the diffusing reflector positioned relative to the transmissive window to not obscure light incident on the transmissive window at a right angle to the transmissive window;
measuring the intensity of the diffused radiation signal on a side opposite to the first surface of the transmissive window; and
detecting foreign particles on the at least one of the first surface or the second surface of the transmissive window based on the measured intensity of the diffused radiation signal.

19. The method of claim 18, wherein directing the first beam of electromagnetic energy at the diffusing reflector includes using a radiation source controlled by a controller having a processor and a memory; and
wherein detecting foreign particles includes using a photoelectric detector generating a radiation signal and supplying the radiation signal to the controller.

20. The method of claim 18, further comprising:
determining a benchmark intensity value, including:
obtaining an expected intensity of the diffused radiation signal if the diffused radiation were to propagate through a region of the transmissive window free of foreign particles; and
selecting the benchmark intensity value based on the obtained expected intensity;
wherein detecting foreign particles includes generating a signal indicative of a presence of foreign particles in a first region of the transmissive window if the measured diffused radiation signal corresponding to the first region is lower than the benchmark intensity value.

21. The method of claim 18, further comprising:
defining a plurality of non-overlapping regions of the transmissive window;
wherein measuring the intensity of the diffused radiation signal includes obtaining a measurement for each of the plurality of non-overlapping regions; and
wherein detecting foreign particles on the at least one of the first surface or the second surface of the transmissive window includes separately analyzing each of the plurality of regions.

22. The method of claim 18, wherein directing the first beam of electromagnetic energy at the diffusing reflector includes directing the first beam through the transmissive window so that the first beam impinges on the second surface of the transmissive window prior to impinging on the diffusing reflector.

23. The method of claim 18, wherein directing the first beam of electromagnetic energy at the diffusing reflector includes generating an electromagnetic wave having a first wavelength; the method further comprising:
directing a second beam of electromagnetic energy at the diffusing reflector, including generating an electromagnetic wave having a second wavelength;
wherein measuring the intensity of the diffused radiation signal includes obtaining a first measurement corresponding to the first beam and obtaining a second measurement corresponding to the second beam; and
wherein detecting foreign particles includes using a ratio of the first measurement and the second measurement.

24. The method of claim 23, wherein the first beam and the second beam are activated in quick succession.

25. A foreign-particle detection system for use with an optical instrument having a transmissive window with a first side and a second side, the system comprising:
a radiation source to generate a first electromagnetic radiation signal of a first wavelength and a second electromagnetic radiation signal of a second wavelength distinct from the first wavelength;
a radiation detector to detect the first electromagnetic radiation signal propagated through the transmissive window, and the second electromagnetic radiation signal propagated through the transmissive window; and
a controller communicatively coupled to the radiation detector to detect a presence of foreign particles on at least one of the first side or the second side of the transmissive window based on a ratio of the intensity of the first electromagnetic radiation signal to the intensity of the second electromagnetic radiation signal.

26. The system of claim 25, wherein the controller is further communicatively coupled to the radiation source to successively activate the first electromagnetic radiation signal and the second electromagnetic radiation signal.

27. The system of claim 25, wherein the radiation source includes a first LED to emit the first signal and a second LED to emit the second signal.

28. The system of claim 25, further comprising a modulator to modulate the first electromagnetic radiation signal and the second electromagnetic radiation signal;
wherein the controller demodulates the first electromagnetic radiation signal and the second electromagnetic radiation signal detected by the radiation detector to separate the first electromagnetic radiation signal and the second electromagnetic radiation signal from ambient noise.

29. The system of claim 25, further comprising a diffusive reflector to diffusively spread the first electromagnetic radiation signal and the second electromagnetic radiation signal over substantially an entire surface of the transmissive window.

30. A method of detecting foreign particles on a surface of a transmissive window of an optical instrument, comprising:
propagating a first radiation signal having a first wavelength through the transmissive window, wherein the first radiation signal impinges on a first side of the transmissive window;
propagating a second radiation signal having a second wavelength through the transmissive window, wherein the second radiation signal impinges on the first side of the transmissive window; and wherein the first radiation signal and the second radiation signal are not propagated simultaneously;
obtaining a first measurement of radiation intensity corresponding to the first radiation signal exiting a second side of the transmissive window;
obtaining a second measurement of radiation intensity corresponding to the second radiation signal exiting on the second side of the transmissive window;

calculating the ratio between the first measurement and the second measurement to detect a presence of foreign particles on the first side or the second side of the transmissive window.

31. The method of claim 30, wherein propagating the first radiation signal and the second radiation signal includes controlling a radiation source from a controller having a processor and a memory; wherein the memory stores a benchmark ratio; and wherein the controller detects a presence of foreign particles by comparing the calculated ratio between the first measurement and the second measurement to the benchmark ratio.

32. The method of claim 30, further comprising generating an alarm signal if foreign particles are detected.

* * * * *